(12) United States Patent  
Kunze et al.

(10) Patent No.: US 7,653,171 B2  
(45) Date of Patent: Jan. 26, 2010

(54) METHOD FOR IMAGE RECONSTRUCTION OF AN OBJECT WITH THE AID OF PROJECTIONS, AND APPARATUS FOR CARRYING OUT THE METHOD

(75) Inventors: Holger Kunze, Bubenreuth (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 237 days.

(21) Appl. No.: 11/806,166

(22) Filed: May 30, 2007

(65) Prior Publication Data

US 2007/0280407 A1   Dec. 6, 2007

(30) Foreign Application Priority Data

May 31, 2006   (DE) ...................... 10 2006 025 759

(51) Int. Cl.  
*A61B 6/03* (2006.01)

(52) U.S. Cl. .............................. 378/4; 378/19
(58) Field of Classification Search ................ 378/4, 378/19; 324/307, 309; 250/363.01, 363.02, 250/363.04, 363.07; 600/425, 437  
See application file for complete search history.

(56) References Cited

U.S. PATENT DOCUMENTS

| | | | |
|---|---|---|---|
| 5,053,958 A | | 10/1991 | Tam |
| 5,331,552 A | * | 7/1994 | Lloyd et al. ................... 378/15 |
| 6,442,288 B1 | | 8/2002 | Haerer et al. |
| 6,810,102 B2 | * | 10/2004 | Hsieh et al. ..................... 378/4 |
| 2005/0111611 A1 | * | 5/2005 | Hein et al. ..................... 378/15 |
| 2005/0111623 A1 | * | 5/2005 | Bruder et al. ................. 378/95 |
| 2006/0062443 A1 | * | 3/2006 | Basu et al. .................. 382/131 |

(Continued)

FOREIGN PATENT DOCUMENTS

DE       39 18 354       1/1990

(Continued)

OTHER PUBLICATIONS

Joseph, Peter M., "An Improved Algorithm for Reprojecting Rays through Pixel Images", IEEE Transactions on Medical Imaging, vol. 1, Issue 3, (Nov. 1982), pp. 192-196.*

(Continued)

*Primary Examiner*—Chih-Cheng G Kao  
(74) *Attorney, Agent, or Firm*—Harness, Dickey & Pierce, P.L.C.

(57) ABSTRACT

A method is disclosed for image reconstruction of an object with the aid of at least one-dimensional projections of the object into a three-dimensional volume image data record, it being possible to generate the projections by at least one detector/source system with reference to different positions and angles relative to the object, and at least two projections forming a reconstruction volume in an overlap region as basis for a backprojection of the projections into the three-dimensional volume image data record, in particular computed tomography. An apparatus for carrying out the method is further disclosed. In at least one embodiment, supplemented reconstruction volumes are generated by supplementing reconstruction volumes, covered only partially by projections, by way of virtual projections that are derived from volume image data records. By comparison with reconstruction volumes that are merely interpolated, supplementing a reconstruction volume with the aid of virtual projections can decisively improve the image quality of the computed tomography images that are backprojected therefrom.

24 Claims, 2 Drawing Sheets

U.S. PATENT DOCUMENTS

2007/0098136 A1    5/2007    Lutz

FOREIGN PATENT DOCUMENTS

| DE | 39 18 354 A1 | 1/1990 |
| DE | 198 42 944 | 7/1997 |
| DE | 19842944 A1 | 7/1999 |
| DE | 103 45 705 | 9/2004 |
| DE | 103 45 705 A1 | 9/2004 |
| DE | 10 2005 037 368 | 2/2007 |
| DE | 10 2005 037 368 A1 | 2/2007 |

OTHER PUBLICATIONS

Hefferman, P.; Robb, R.: Image Reconstruction from Incomplete Data: Iterative Reconstruction-Reprojection Techniques. IEEE Trans. on Biomedical Engineering, vol. 30, No. 12, Dec. 1983, pp. 838-841.

Kak, Avinash C. and Malcolm Slaney. "Principles of Computerized Tomographic Imaging. Electronic Copy". IEEE Press. 1999.

* cited by examiner

METHOD FOR IMAGE RECONSTRUCTION OF AN OBJECT WITH THE AID OF PROJECTIONS, AND APPARATUS FOR CARRYING OUT THE METHOD

PRIORITY STATEMENT

The present application hereby claims priority under 35 U.S.C. §119 on German patent application number DE 10 2006 025 759.6 filed May 31, 2006, the entire contents of which is hereby incorporated herein by reference.

FIELD

Embodiments of the invention generally relate to a method for image reconstruction of an object with the aid of at least one-dimensional projections of the object into a three-dimensional volume image data record. For example, in at least one embodiment, it is possible to generate the projections by at least one detector/source system with reference to different positions and angles relative to the object, and at least two projections forming a reconstruction volume in an overlap region as basis for a backprojection of the projections into the three-dimensional volume image data record. Embodiments of the invention likewise generally relate to an apparatus for carrying out the method.

BACKGROUND

Medical image recording methods require a multiplicity of processing steps for the images of an object to be examined that are generated mostly by a detector/source system. In this case, the detector/source system records projections of the radiation attenuated by the object with reference to different angles. These projections can be used to derive in the overlap region of the projections a so-called reconstruction volume that is a precondition for the backprojection into a three-dimensional volume image data record of the object.

The basis of the medical image recording methods is provided here by image projection and image transformation methods that combine the recorded projections on the basis of the orientation of the detector/source system during a projection recording with the orientation-dependent attenuation of the respective radiation by the object to be examined to form a reconstruction volume, and subsequently backproject it as images. The spatially dependent attenuation values thus determined then serve as basis for the backprojection into the volume image data record. In order to record the projections of the object to be examined, such as, for example, the body of a patient, radiation sources and correspondingly arranged radiation detectors are frequently arranged for transirradiating the object. The object to be transirradiated, or subregions of the object, characteristically attenuate the radiation emitted by the radiation source, characteristic projections of the attenuation profile respectively being determined in the radiation detector as a function of the relative position and distance of the radiation source and the radiation detector in relation to the object.

A line integral can respectively be formed relative to the object for each beam profile on the basis of the known angular dependence of the detected projections by means of the so-called Radon transformation. In the overlap region of the projections, the line integrals form the reconstruction volume that serves as database for a subsequent backprojection into the three-dimensional volume image data record.

The backprojection of the reconstruction volume in relation to a volume image data record is frequently performed by way of a so-called inverse Radon transformation. The Fourier slice theorem or a filtered backprojection is frequently used for this purpose. The filtered backprojection is mostly used in medical image recording systems because of the high numerical stability. The medical images can subsequently be extracted from this volume image data record thus generated, doing so with reference to freely selectable image planes.

For the purpose of completely covering a three-dimensional image data record, it is necessary, moreover, to determine inside the overlap region the data points that are not covered by the overlapping of at least two projections in an overlap region.

Currently, the missing data points inside the overlap region are interpolated by way of additional projection data from additional detectors on the basis of the projection data of the largest detector. Only in the case of complete coverage of the overlap region of all the beam profiles is a filtered backprojection of the projections of the attenuation profiles possible. Moreover, it is necessary to take account in the case of the backprojection of the type of projection, for example a parallel projection or a fan projection.

In order to generate an interpolated reconstruction volume, recording the projections therefore frequently requires a particularly high rotational speed for the detector/source system rotating by 360° or 180° on a circular path, in order to obtain a complete image of the object to be examined within a short time period. In particular, pictures of moving organs of a patient such as, for example, pictures of the lung or of the heart, must be recorded within a very short time interval, since otherwise the movement of the organ would distort the medical images. The conventional approach is to use a number of detector/source systems fitted in an offset fashion in the direction of rotation in order to generate the projections during a revolution, and subsequently to combine the projections by way of image projection and image transformation methods, and to backproject them into a three-dimensional volume image data record.

During the generation of the projections, in commonly used image recording systems two detector/source systems move about the object to be examined, the relative position of the two systems in relation to one another remaining the same during the recordings. For reasons of cost and space, it is often customary to give the second and the further detectors smaller design dimensions than the main detector of the first detector/source system such that the overlap region of all the beam profiles of the two detector/source system does not detect the entire object to be examined, or the overlap region thus produced is smaller than in the case of detectors of a multidetector/source system that have the same dimensions.

An additional complicated factor here is that a mathematical stipulation of the filtered backprojection of the reconstruction volume enables a complete overlapping of all the beam profiles only when all the data points of the reconstruction volume are determined. In particular, in the case of multidetector/source systems with different detector sizes, the problem arises of an overlap region that is reduced and covered by projections only incompletely in part by comparison with multidetector/source systems of the same detector size.

The problem is currently solved by determining the projections with the aid of a two-fold detector/source system, the first detector/source system having a large detector, and the second detector/source system having a smaller detector. While taking account of the projections of the first detector/source system, the data points inside the reconstruction volume of the additional detector/source systems are interpolated by considering adjacent line integrals inside the overlap regions covered only partially by projections. The reconstruction volume thus mathematically completed is subsequently completely backprojected into a volume image data record by way of a backprojection. No comparison currently exists with measured data for the inadequately covered data points of the only partially covered overlap regions.

Subsequently, it is optionally possibly after completion of the abovedescribed image processing method to carry out filtering and image reprocessing of the image points in the reconstruction volume and/or of the medical images thus generated.

Thus, DE 198 42 944 A1 describes a method for the reconstruction of a three-dimensional image of an object scanned in the course of a tomosynthesis, as well as an apparatus for the tomosynthesis. By selecting two- and three-dimensional filter functions for the reconstruction volume by taking account of suitable weighting elements and optimized filters, the invention mentioned there provides the possibility of improving the image quality and—for the slicewise display of the volume image data record—of reducing high frequency image components.

In the case of all the reconstruction methods known in the prior art, it is disadvantageous for projections that, in order to completely cover the reconstruction volume, mathematical interpolations of data points are undertaken on the basis of adjacent line integrals in the reconstruction volume that can lead during the backprojection to an impairment of the image quality of the volume image data record, as in computed tomography (CT), for example.

SUMMARY

In at least one embodiment, the present invention provides an image recording method that permits a backprojection into a three-dimensional volume image data record even given an overlap region that is covered only partially by projections.

It is provided according to at least one embodiment of the invention, that virtual projections are generated on the basis of an overlap region completely covered by at least a portion of the projections, and the virtual projections are used to supplement at least one overlap region covered only partially by projections.

Within the meaning of at least one embodiment of the invention, a completely covered overlap region is suitable for defining, within the scope of the respectively applied mathematical reconstruction method, a reconstruction volume from which a corresponding three-dimensional volume image data record can be completely backprojected.

An advantage of the method according to at least one embodiment of the invention is that the missing data points in the reconstruction volume are not, as previously, interpolated between two known data points, but are calculated by way of already determined data points of another reconstruction volume. These missing data points in the reconstruction volume covered only partially by projections are supplemented by way of the virtual projections. Since the virtual projections are based on data already measured and not interpolated, this results in fewer artifacts during image reconstruction at the transitions between the measured and supplemented data points by comparison with the transitions, known from the prior art, between measured and interpolated data points.

In an advantageous refinement of at least one embodiment of the method, the completely covered overlap region is determined starting from an initial overlap region, the largest possible, completely covered overlap region being determined iteratively by the addition of relevant projections. The fixing of an initial overlap region ensures that a completely covered overlap region is always fixed as initial point for carrying out the method according to at least one embodiment of the invention.

In many detector/source systems, the rotation axes are arranged such that they run through the central ray (imaginary line from the radiation source to the middle of the detector), and therefore through the isocenter of the image recording system. There is always a complete overlap of the projections in the region of the intersection of the rotation axes of a detector/source system, and so, for example, this overlap region can be defined as initial overlap region. On the basis of this overlap region, further already determined projections are added and an iterative check is made as to whether the further projections enlarge the basic overlap region and the overlap region thus enlarged is completely covered by projections already considered and/or by further projections. Should it be impossible to use the overlap region that has already been determined and is completely covered with projections in order to determine a larger completely covered projection region, the already determined overlap region completely covered with projections is used as basis for forming the first reconstruction volume.

A first reconstruction volume is advantageously generated on the basis of the completely covered overlap region, and a first three-dimensional volume image data record is generated therefrom, the virtual projections subsequently being extracted from the first three-dimensional volume image data record.

The virtual projections are preferably extracted as line integrals from the first three-dimensional volume image data record. The first three-dimensional volume image data record is used as basis for the "virtual projection images" of the part of the recorded object imaged by the three-dimensional volume image data record, the virtual projections being determined as line integrals from the first three-dimensional volume image data record.

In an advantageous refinement of at least one embodiment, it is provided that on the basis of the completely covered overlap region, the first reconstruction volume, and on the basis of the overlap region partially covered with projections, the second reconstruction volume are combined, in a fashion supplemented by the virtual projections, to form a total reconstruction volume, and the three-dimensional total volume image data record is subsequently backprojected from the total reconstruction volume. The combination of the individual reconstruction volumes to form a total reconstruction volume enables the backprojection into a larger three-dimensional volume image data record if one of the reconstruction volumes is not a complete component of the further reconstruction volumes.

It is provided alternatively that on the basis of the first reconstruction volume, the first three-dimensional volume image data record, and on the basis of the second reconstruction volume, which is supplemented by the virtual projections, a second three-dimensional volume image data record are backprojected, and the first three-dimensional volume image data record and the second three-dimensional volume image data record are subsequently combined to form a total volume image data record.

An example refinement of the inventive method provides that the projections are generated by a first detector/source system having a first detector, and at least one second detector/source system having a detector that is smaller by comparison with the first detector. Particularly in the case of imaging methods with short measuring times such as, for example, imaging of the lung or of the heart, a particularly high rotational speed is required for the multidetector/source system. These high rotational speeds are mostly achieved by using a number of detector/source systems fitted in a fashion offset in the direction of rotation. The method according to the invention can therefore be used in particular in the case of existing image recording systems having different detector sizes.

In an advantageous refinement of an embodiment of the method, it is provided that the projections of the first detector/source system are used to form the completely covered overlap region, and virtual projections are subsequently used therefrom. to supplement the projections of the second detector/source system.

The backprojection of the projections into the three-dimensional volume image data record is preferably a filtered backprojection. The image recording method on which the detector/source system is based is advantageously an X-ray tomography method, a magnetic resonance imaging method, an emission tomography method, in particular a positron emission tomography method (PET method), an optical tomography method, a quantum tomography method and/or an impedance tomography method. The image recording method is preferably controlled by way of a computer unit. In an example refinement of the method, the three-dimensional volume image data record is used to extract plane images with reference to freely selectable image planes from the three-dimensional volume image data record.

It is provided according to an embodiment of the invention that at least one detector/source system and a computer unit, in particular freely programmable logic modules (Field Programmable Gate Arrays, abbreviated: FPGAs) or application-specific integrated circuits (abbreviated: ASICs) carry out the calculations of the virtual projections. In an advantageous refinement of the apparatus, it is provided that a first detector/source system, having a first detector, and at least one second detector/source system having a detector that is smaller by comparison with the first detector, generate the projections.

Further advantageous refinements of the present invention follow from the subclaims.

BRIEF DESCRIPTION OF THE DRAWINGS

The invention is explained in more detail below with aid of example embodiments. By way of example, in the drawings.

DETAILED DESCRIPTION OF THE EXAMPLE EMBODIMENTS

Figure 1:
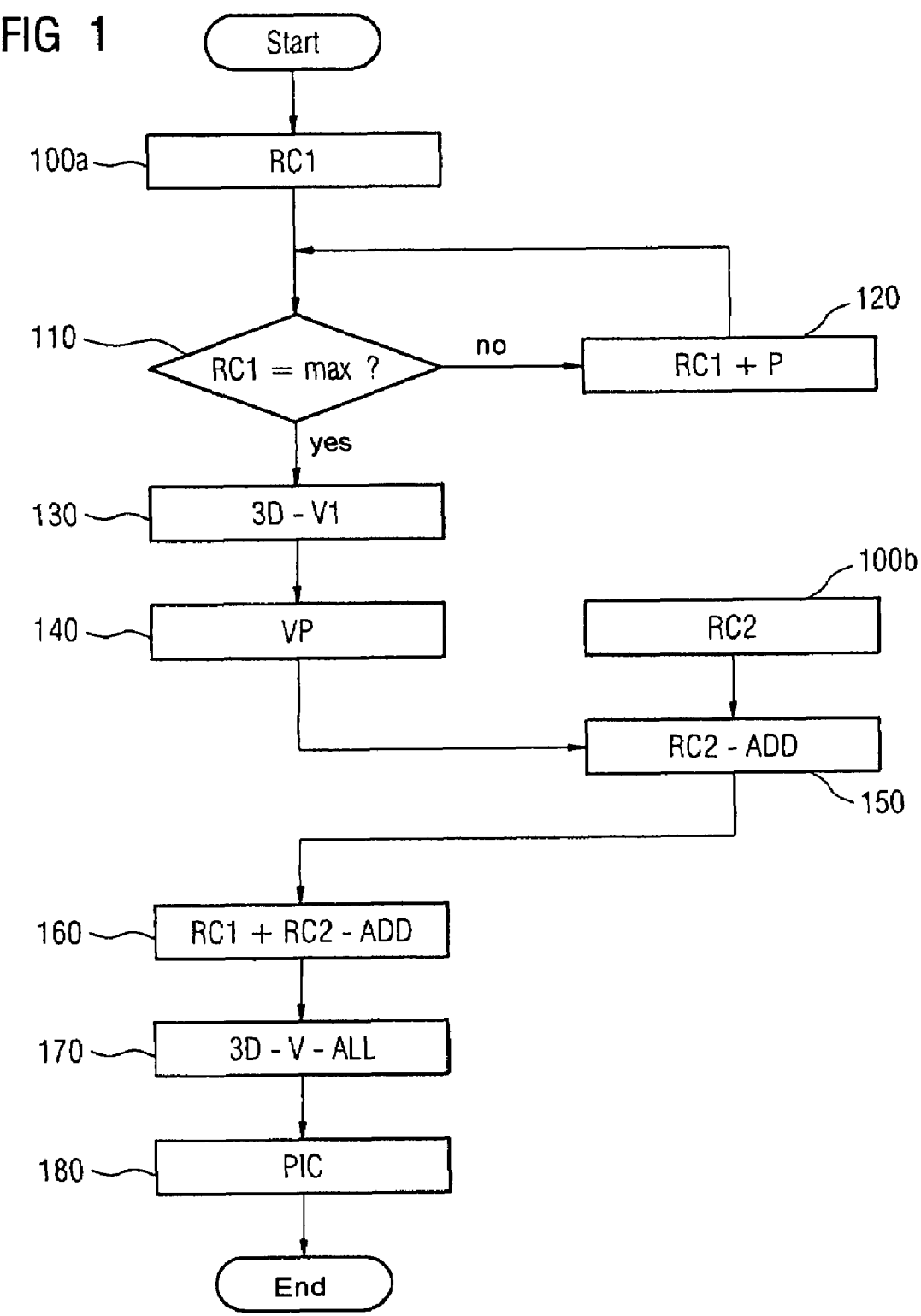
FIG. 1 shows a flowchart of the method according to an embodiment of the invention with a combination of the first reconstruction volume and the supplemented second reconstruction volume.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows a flowchart of the method according to an embodiment of the invention with a combination of the first initial overlap region 100a and the supplemented second overlap region 150 to form a total reconstruction volume 160. The initial overlap region 100a ensures a complete coverage of the projections inside the overlap region 100a. On the basis of interrogation 110, either the initial overlap region 100a is expanded, by means of additions 120, by further relevant projections—designated by P in FIG. 1—or is used as initial point for a backprojection into a first three-dimensional volume image data record 130.

Subsequently, there are extracted from the first three-dimensional volume image data record 130 virtual projections 140 that serve to supplement 150 at least one second overlap region 100b having only partial projection coverage. The overlap regions 100a and 150 are then combined to form a total reconstruction volume 160. A three-dimensional total volume image data record 170 is then generated by way of a filtered backprojection on the basis of the total reconstruction volume 160. Medical images 180 can then be extracted from the three-dimensional total volume image data record 170 with reference to arbitrary image planes inside the three-dimensional total volume image data record 170, and subsequently visualized.

Figure 2:
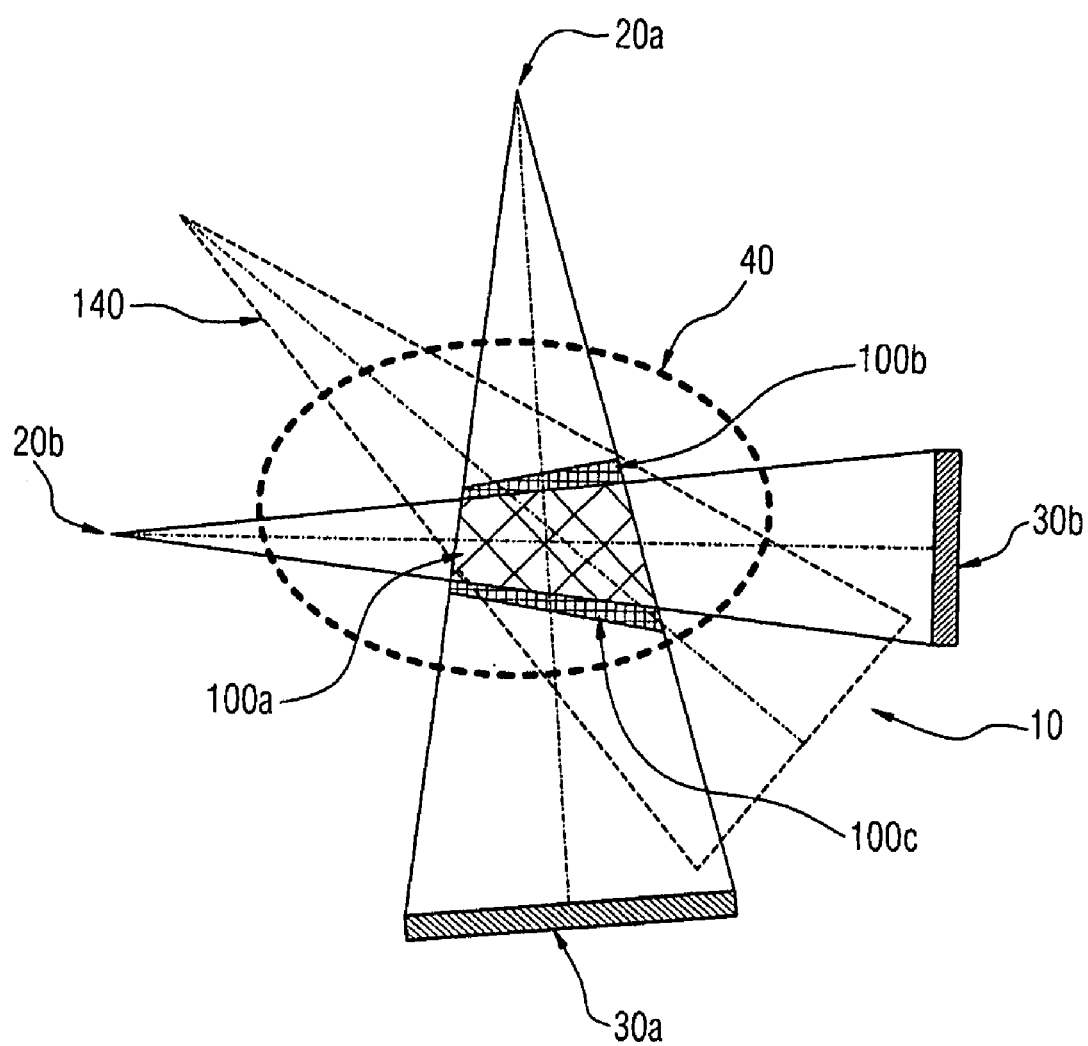
FIG. 2 shows an image recording system having two detector/source systems with a first overlap region and two further overlap regions covered only partially by the projections.

FIG. 2 shows an inventive image recording system 10 having two detector/source systems with a first overlap region 100a, completely covered by projections, and two further overlap regions 100b, 100c, covered only partially by the projections. A first detector/source system 20a, 30a and a second detector/source system 20b, 30b are arranged around the object 40, for example a patient, such that the object 40 is located at least partially in the isocenter of the respective detector/source systems 20a, 30a; 20b, 30b. The second detector/source system 20b, 30b has a smaller detector 30b by comparison with the first detector 30a. The overlap region 100a of a complete projection coverage serves to generate an intermediate image from which virtual projections 140 are then extracted to supplement the as of yet not completely covered overlap regions 100b, 100c.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for image reconstruction of an object with the aid of at least one-dimensional projections of the object into a three-dimensional volume image data record, the projections being generated by at least one detector/source system with reference to different positions and angles relative to the object, and at least two of the projections forming a reconstruction volume in an overlap region as the basis for a backprojection of the projections into the three-dimensional volume image data record, the method comprising:

generating virtual projections based upon an overlap region completely covered by at least a portion of the projections; and using the virtual projections to supplement at least one overlap region covered only partially by the projections, wherein the completely covered overlap region is determined starting from an initial overlap region, a largest possible completely covered overlap region being determined iteratively by the addition of relevant projections.

2. The method as claimed in claim 1, wherein a first reconstruction volume is generated on the basis of the completely covered overlap region, and a first three-dimensional volume image data record is generated therefrom, the virtual projections subsequently being extracted from the first three-dimensional volume image data record.

3. The method as claimed in claim 2, wherein the virtual projections are extracted as line integrals from the first three-dimensional volume image data record.

4. The method as claimed in claim 1, wherein, on the basis of the completely covered overlap region, a first reconstruction volume, and on the basis of the partially covered overlap region, a second reconstruction volume are combined, in a fashion supplemented by the virtual projections, to form a total reconstruction volume, and a three-dimensional total volume image data record is subsequently backprojected from the total reconstruction volume.

5. The method as claimed in claim 4, wherein, on the basis of the first reconstruction volume, a first three-dimensional volume image data record, and on the basis of the second reconstruction volume, a second three-dimensional volume image data record are backprojected, and wherein the first three-dimensional volume image data record and the second three-dimensional volume image data record are subsequently combined to form the three-dimensional total volume image data record.

6. The method as claimed in claim 5, wherein the projections are generated by a first detector/source system having a first detector, and at least one second detector/source system having a detector that is relatively smaller than the first detector.

7. The method as claimed in claim 5, wherein the image recording method on which the detector/source system is based is at least one of an X-ray tomography method, a magnetic resonance imaging method, an emission tomography method, an optical tomography method, a quantum tomography method and an impedance tomography method.

8. The method as claimed in claim 4, wherein the backprojection of the projections into the three-dimensional volume image data record is a filtered backprojection.

9. The method as claimed in claim 1, wherein the projections are generated by a first detector/source system having a first detector, and at least one second detector/source system having a detector that is relatively smaller than the first detector.

10. The method as claimed in claim 9, wherein the projections of the first detector/source system are used to form the completely covered overlap region, and virtual projections are subsequently used therefrom to supplement the projections of the second detector/source system.

11. The method as claimed in claim 1, wherein the image recording method on which the detector/source system is based is at least one of an X-ray tomography method, a magnetic resonance imaging method, an emission tomography method, an optical tomography method, a quantum tomography method and an impedance tomography method.

12. The method as claimed in claim 1, wherein the image recording method is controlled by a computer unit.

13. The method as claimed in claim 1, wherein the three-dimensional volume image data record is used to extract plane images with reference to freely selectable image planes from the three-dimensional volume image data record.

14. An apparatus, comprising at least one detector/source system; and a computing unit configured to carry out the method as claimed in claim 1.

15. The apparatus as claimed in claim 14, wherein at least one of freely programmable logic modules (FPGAs) and application-specific integrated circuits (ASICs) carry out calculation of the virtual projections, and the overlap region covered only partially by projections is supplemented by the virtual projections.

16. The apparatus as claimed in claim 15, wherein the at least one detector/source system includes a first detector/source system having a first detector, and at least one second detector/source system having a detector, the detector of the at least one second detector/source being relatively smaller than the detector of the at least one first detector/source.

17. The apparatus as claimed in claim 14, wherein the at least one detector/source system includes a first detector/source system having a first detector, and at least one second detector/source system having a detector, the detector of the at least one second detector/source being relatively smaller than the detector of the at least one first detector/source.

18. An apparatus, comprising:
   at least one detector/source system that records projections with reference to different positions and angles relative to an object, at least two projections forming a reconstruction volume in an overlap region as basis for a backprojection of the projections into the three-dimensional volume image data record;
   means for generating virtual projections based upon an overlap region completely covered by at least a portion of the projections; and
   means for using the virtual projections to supplement at the least one overlap region covered only partially by the projections, wherein
   the completely covered overlap region is determined starting from an initial overlap region, a largest possible completely covered overlap region being determined iteratively by the addition of relevant projections.

19. The apparatus as claimed in claim 18, wherein a first reconstruction volume is generated on the basis of the completely covered overlap region, and a first three-dimensional volume image data record is generated therefrom, the virtual projections subsequently being extracted from the first three-dimensional volume image data record.

20. The apparatus as claimed in claim 19, wherein the virtual projections are extracted as line integrals from the first three-dimensional volume image data record.

21. The apparatus as claimed in claim 20, wherein, on the basis of the completely covered overlap region, the first reconstruction volume, and on the basis of the partially covered overlap region, a second reconstruction volume are combined, in a fashion supplemented by the virtual projections, to form a total reconstruction volume, and the three-dimensional total volume image data record is subsequently backprojected from the total reconstruction volume.

22. The apparatus as claimed in claim 18, wherein the means for generating and means for using include at least one of freely programmable logic modules (FPGAs) and application-specific integrated circuits (ASICs) to carry out a calculation of the virtual projections, and wherein the overlap region covered only partially by projections is supplemented by the virtual projections.

23. The apparatus as claimed in claim 22, wherein the at least one detector/source system includes a first detector/source system having a first detector, and at least one second detector/source system having a detector, the detector of the at least one second detector/source being relatively smaller than the detector of the at least one first detector/source.

24. The apparatus as claimed in claim 18, wherein the at least one detector/source system includes a first detector/source system having a first detector, and at least one second detector/source system having a detector, the detector of the at least one second detector/source being relatively smaller than the detector of the at least one first detector/source.

* * * * *